(12) United States Patent
LaBeaume et al.

(10) Patent No.: US 10,042,251 B2
(45) Date of Patent: Aug. 7, 2018

(54) ZWITTERIONIC PHOTO-DESTROYABLE QUENCHERS

(71) Applicant: Rohm and Haas Electronic Materials LLC, Marlborough, MA (US)

(72) Inventors: Paul J. LaBeaume, Auburn, MA (US); James F. Cameron, Brookline, MA (US)

(73) Assignee: ROHM AND HAAS ELECTRONIC MATERIALS LLC, Marlborough, MA (US)

( * ) Notice: Subject to any disclaimer, the term of this patent is extended or adjusted under 35 U.S.C. 154(b) by 0 days.

(21) Appl. No.: 15/281,683

(22) Filed: Sep. 30, 2016

(65) Prior Publication Data

US 2018/0095364 A1  Apr. 5, 2018

(51) Int. Cl.
| | | |
|---|---|---|
| G03F 7/004 | (2006.01) | |
| C07D 333/76 | (2006.01) | |
| G03F 7/32 | (2006.01) | |
| G03F 7/38 | (2006.01) | |
| H01L 21/027 | (2006.01) | |
| C07C 381/12 | (2006.01) | |
| C07C 309/12 | (2006.01) | |
| G03F 7/039 | (2006.01) | |

(52) U.S. Cl.
CPC .......... G03F 7/0045 (2013.01); C07C 309/12 (2013.01); C07C 381/12 (2013.01); C07D 333/76 (2013.01); G03F 7/0397 (2013.01); G03F 7/32 (2013.01); G03F 7/38 (2013.01); H01L 21/0274 (2013.01); C07C 2603/74 (2017.05); G03F 7/0046 (2013.01)

(58) Field of Classification Search
CPC ... G03F 7/004; G03F 7/20; G03F 7/32; G03F 7/38; G03F 7/40; H01L 21/0274; C07C 381/12
USPC .... 430/270.1, 913, 322, 325, 329, 330, 331; 562/100, 41, 75, 83; 568/34
See application file for complete search history.

(56) References Cited

U.S. PATENT DOCUMENTS

| | | | | |
|---|---|---|---|---|
| 2010/0063302 A1* | 3/2010 | Muraoka | .............. | C07D 327/10 549/18 |
| 2011/0008735 A1* | 1/2011 | Ohsawa | ................. | C07C 381/12 430/326 |
| 2013/0035503 A1* | 2/2013 | Oh | ........................ | C07C 309/06 560/138 |
| 2014/0005301 A1* | 1/2014 | Kunimoto | ............ | C07D 307/10 523/400 |
| 2014/0322650 A1* | 10/2014 | Ohashi | ..................... | G03F 7/038 430/281.1 |
| 2016/0004155 A1* | 1/2016 | Ohashi | .................. | G03F 7/2053 430/270.1 |
| 2016/0320699 A1* | 11/2016 | Yamada | ................ | G03F 7/0045 |
| 2016/0349612 A1* | 12/2016 | Fujiwara | ............... | C08F 220/38 |

FOREIGN PATENT DOCUMENTS

| | | |
|---|---|---|
| JP | 10182631 | 7/1998 |
| WO | 9424122 A1 | 10/1994 |
| WO | 2007061661 A2 | 5/2007 |
| WO | 2008057254 A2 | 5/2008 |
| WO | 2008137816 A2 | 11/2008 |
| WO | 2010125985 A1 | 11/2010 |

OTHER PUBLICATIONS

Li et al. "Identification of an Orally Efficacious Matrix Metalloproteinase 12 Inhibitor for Potential Treatment of Asthma"; J. Med. Chem.; 2009; vol. 52; pp. 5408-5419.
Pegot et al. "Ionic liquids as new media for electrophilic trifluoromethylation reactions"; J. of Fluorine Chem.; 2012; vol. 134; pp. 156-159.
St. Jean, Jr. et al. "2-(S)-Phenethylaminothiazolones as Potent, Orally Efficacious Inhibitors of 11beta-Hydroxysteriod Dehydrogenase Type 1"; J. Med. Chem.; 2007; vol. 50; 429-432.
Umemoto et al. "Effective methods for preparing S-(trifluoromethyl)dibenzothiophenium salts"; J. of Fluorine Chem.; 1999; vol. 98; pp. 181-187.
Umemoto et al. "Effective methods for preparing S-(trifluoromethyl)dibenzothiophenium salts"; J. of Fluorine Chem.; 1999; vol. 98; pp. 75-81.
Umemoto et al. Useful electrophilic trifluoromethylating agents; S-, Se- and Te-(trifluoromethyl) dibenzo-thio-,-seleno- and -tellurophenium-3-sulfonates; J. of Fluorine Chem.; 1995; vol. 74; pp. 77-82.
Umemoto et al. Erratum to "Effective methods for preparing S-(trifluoromethyl)dibenzothiophenium salts" [J. Fluorine Chem. 92 (1998) 181-187]; J. of Fluorine Chem.; 1999; vol. 98; p. 73.
Venugopalan et al. "On the Methyl-Transfer Reaction in Crystalline Methyl 2-(Methylthio)benzenesulfonate: a Thermally Induced Non-Topochemical Solid-State Reaction"; Helvetica Chimica Acta; 1991; vol. 74; pp. 662-669.
Vogt et al. "Synthesis and Properties of 8-Mercaptoquinoline-5-Sulfonic Acid as well as a Number of Its Derivatives"; J. of Practical Chem.; Series 4; vol. 31; pp. 240-262.

\* cited by examiner

*Primary Examiner* — Amanda C. Walke
(74) *Attorney, Agent, or Firm* — Cantor Colburn LLP

(57) ABSTRACT

A photo-destroyable quencher having Formula (I):

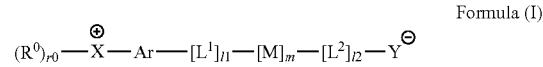

Formula (I)

wherein in Formula (I), groups and variables are the same as described in the specification.

17 Claims, No Drawings

ZWITTERIONIC PHOTO-DESTROYABLE QUENCHERS

FIELD

The present invention relates to photo-destroyable quenchers and their use in photoresist compositions.

INTRODUCTION

Advanced lithographic techniques such as electron beam and extreme ultraviolet lithography have been developed to achieve high quality and smaller feature sizes in microlithography processes, for purposes of forming ever-smaller logic and memory transistors. These advanced lithographic techniques use photoresist compositions, which often include photoacid generators. Photoacid generators generate acid on exposure to incident radiation. In exposed areas of a photoresist, the generated acid reacts with acid-sensitive groups in a photoresist polymer to change the solubility of the polymer, thereby creating a difference in solubility between the exposed and unexposed regions of the photoresist.

Photoresists sometimes include photo-destroyable quenchers in addition to photoacid generators. Like photoacid generators, photo-destroyable quenchers generate acid in exposed areas of a photoresist, but the acid generated by a photo-destroyable quencher is not strong enough to react rapidly with the acid-sensitive groups on the photoresist polymer (this is what effectively removes the "base" component in the exposed region but leaves an active quencher system in the unexposed area). However, as the strong acid generated by the photoacid generator in the exposed region migrates to the unexposed region, the photo-destroyable quencher in the unexposed region undergoes an anion exchange, losing the anion (conjugate base) of the weak acid, and gaining the anion (conjugate base) of the strong acid. This results in neutralization of the strong acid in the unexposed region. So, the concentration of the base is lowered in the exposed region because the photo-destroyable quencher is destroyed in that region. Accordingly, the concentration of the conjugate base anion is lower in the exposed region than in the unexposed region, which helps the image contrast.

Resist formulations containing photo destroyable quenchers are known to improve line width roughness without sacrifice to resolution and sensitivity. Conventional photo-destroyable quenchers are sulfonium salts which have the same cation but a different (and much weaker) conjugate base anion from the photo acid generators in the formulation. As such, any metathesis that would occur between the two salt pairs in the formulation would not influence the total landscape, or makeup of the concentration of photoacid generators versus photo-destroyable quenchers.

As feature size continues to shrink, the need for further improvement in line width roughness is desired, and scientists are beginning to look deeper into the photo-destroyable quencher concept for the answer. One potential solution to improve line width roughness might be using a sulfonium photo-destroyable quencher which has a different cation and anion from the sulfonium photoacid generator. However, this presents a significant problem as metathesis between these two salts may occur within the formulation, fully or partially negating the intended individual purpose of each compound.

Therefore, there remains a need in structurally novel photo-destroyable quenchers which can avoid salt exchange in the formulation with photoacid generators.

SUMMARY

An embodiment provides a photo-destroyable quencher having Formula (I):

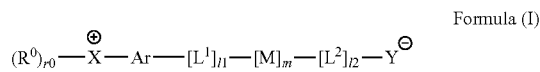

Formula (I)

wherein each $R^0$ is attached to X, and is independently a $C_{1-30}$ alkyl group, a polycyclic or monocyclic $C_{3-30}$ cycloalkyl group, a polycyclic or monocyclic $C_{6-30}$ aryl group, or a combination comprising at least one of the foregoing, provided that at least one $R^0$ is a polycyclic or monocyclic $C_{6-30}$ aryl group;

r0 is 1 or 2, provided that when X is I, r0 is 1, and when X is S, r0 is 2, wherein when X is S, groups $R^0$ are optionally connected to each other so as to form a ring; and Ar is a substituted or unsubstituted divalent $C_6$-$C_{30}$ aromatic group;

$L^1$ and $L^2$ are each independently a divalent $C_1$-$C_{30}$ linking group optionally comprising a heteroatom comprising O, S, N, F, or a combination comprising at least one of the foregoing heteroatoms;

M is a substituted or unsubstituted, divalent $C_5$-$C_{30}$ or greater monocyclic, polycyclic, or fused polycyclic cycloaliphatic group, optionally comprising a heteroatom comprising O, S, N, F, or a combination comprising at least one of the foregoing;

Y is an oxygen-containing anionic group; and $l_1$, $l_2$, and m are each independently an integer of 0 or 1.

Another embodiment provides a composition including the compound including:

an acid-sensitive polymer;

a photoacid generator; and a photo-destroyable quencher having Formula (I).

Still another embodiment provides a coated substrate including: (a) a substrate having one or more layers to be patterned on a surface thereof; and (b) a layer of the composition disposed over the one or more layers to be patterned.

Yet another embodiment provides a method of making a relief image, the method including:

coating a substrate having a layer comprising a photoacid generator and a photo-destroyable quencher having Formula (I), pattern-wise exposing the composition layer to radiation; and developing the pattern by treatment with an aqueous alkaline developer to form a positive tone relief image, or with an organic solvent developer to form a negative tone relief image.

DETAILED DESCRIPTION

Reference will now be made in detail to the exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present inventive concept. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third, etc., may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, when a definition is not otherwise provided, the term "alkyl group" refers to a group derived from a straight or branched chain saturated aliphatic hydrocarbon having the specified number of carbon atoms and having a valence of at least one.

As used herein, when a definition is not otherwise provided, the term "fluoroalkyl group" refers to an alkyl group in which at least one hydrogen atom is replaced with a fluorine atom.

As used herein, when a definition is not otherwise provided, the term "alkoxy group" refers to "alkyl-O—", wherein the term "alkyl" has the same meaning as described above.

As used herein, when a definition is not otherwise provided, the term "fluoroalkoxy group" refers to an alkoxy group in at least one hydrogen atom that is replaced with a fluorine atom.

As used herein, when a definition is not otherwise provided, the term "alkenyl group" refers to a group derived from a straight or branched chain unsaturated aliphatic hydrocarbon having the specified number of carbon atoms and having a valence of at least one.

As used herein, when a definition is not otherwise provided, the term "cycloalkyl group" refers to a monovalent group having one or more saturated rings in which all ring members are carbon.

As used herein, when a definition is not otherwise provided, the term "fluorocycloalkyl group" refers to a cycloalkyl group in which at least one hydrogen atom is replaced with a fluorine atom.

As used herein, when a definition is not otherwise provided, the term "aryl group", which is used alone or in combination, refers to an aromatic hydrocarbon containing at least one ring and having the specified number of carbon atoms. The term "aryl" may be construed as including a group with an aromatic ring fused to at least one cycloalkyl ring.

As used herein, when a definition is not otherwise provided, the term "aralkyl group" refers to a substituted or unsubstituted aryl group covalently linked to an alkyl group that is linked to a compound, wherein the terms "aryl" and "alkyl" have the same meaning as described above.

As used herein, when a definition is not otherwise provided, the term "substituted" means including at least one substituent such as a halogen (F, Cl, Br, I), hydroxyl, amino, thiol, carboxyl, carboxylate, ester (including acrylates, methacrylates, and lactones), amide, nitrile, sulfide, disulfide, nitro, $C_{1-20}$ alkyl, $C_{1-20}$ cycloalkyl (including adamantyl), $C_{1-20}$ alkenyl (including norbornenyl), $C_{1-20}$ alkoxy, $C_{2-20}$ alkenoxy (including vinyl ether), $C_{6-30}$ aryl, $C_{6-30}$ aryloxy, $C_{7-30}$ alkylaryl, or $C_{7-30}$ alkylaryloxy.

When a group containing a specified number of carbon atoms is substituted with any of the groups listed in the preceding paragraphs, the number of carbon atoms in the resulting "substituted" group is defined as the sum of the carbon atoms contained in the original (unsubstituted) group and the carbon atoms (if any) contained in the substituent. For example, when the term "substituted $C_1$-$C_{20}$ alkyl" refers to a $C_1$-$C_{20}$ alkyl group substituted with $C_6$-$C_{30}$ aryl group, the total number of carbon atoms in the resulting aryl substituted alkyl group is $C_7$-$C_{50}$.

As used herein, when the definition is not otherwise provided, the term "mixture" refers to any combination of the ingredients constituting the blend or mixture without regard to a physical form.

As noted above, there is currently a need in structurally novel photo-destroyable quenchers which can avoid salt exchange in the formulation with photoacid generators. The current invention presents novel photo-destroyable quenchers which have the anion and cation covalently bound to each other to form a zwitterionic species or a "fused photo-destroyable quenchers". These novel photo-destroyable quenchers are unable to undergo salt exchange with any other salt (namely, the sulfonium or iodonium photoacid generator) in a formulation. This novel technology allows for both the cation and anion of a given photo-destroyable quencher to be optimized for a specific purpose/formulation without sacrifice to the integrity of the photoacid generator in a given system.

Disclosed herein is a zwitterionic photo-destroyable quencher represented by Formula (I):

Formula (I)

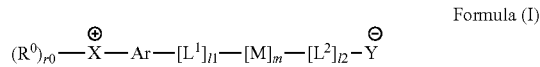

In Formula (I), X may be sulfur (S) or iodine (I). Groups R⁰ may be the same or different, and may each independently be a $C_{1-30}$ alkyl group, a polycyclic or monocyclic $C_{3-30}$ cycloalkyl group, a polycyclic or monocyclic $C_{6-30}$ aryl group, or a combination comprising at least one of the foregoing, provided that at least one R⁰ is a polycyclic or monocyclic $C_{6-30}$ aryl group.

r0 may be 1 or 2. When, X is I, r0 is 1. When X is S, r0 is 2. When X is S, one of R⁰ may be a polycyclic or monocyclic $C_{6-30}$ aryl group, while the other one of R⁰ may be a $C_{1-30}$ alkyl group, a polycyclic or monocyclic $C_{3-30}$ cycloalkyl group, or a polycyclic or monocyclic $C_{6-30}$ aryl group. When X is S, groups R⁰ may be optionally connected to each other so as to form a ring. In an embodiment, each R⁰ may be a polycyclic or monocyclic $C_{6-30}$ aryl group.

Ar may be a substituted or unsubstituted divalent $C_6$-$C_{30}$ aromatic group. The divalent $C_6$-$C_{30}$ aromatic group may include a single aromatic ring or more than one aromatic ring. When the divalent $C_6$-$C_{30}$ aromatic group includes more than one aromatic ring, the rings may be fused or may be connected by a single bond. In an embodiment, Ar may be a substituted or unsubstituted phenylene group.

The zwitterionic photo-destroyable quencher represented by Formula (I) may further include linking groups $L^1$, M, and $L^2$.

$L^1$ and $L^2$ may each independently be a divalent $C_1$-$C_{30}$ linking group, and may include a heteroatom selected from O, S, N, F, or a combination of at least one of these heteroatoms. When l1 is 1, the linking group $L^1$ is present. When l1 is 0, the linking group $L^1$ is absent. When $L^1$ is absent, group Ar may be directly connected to the linking group M via a single bond. Likewise, when l2 is 1, the linking group $L^2$ is present. When l2 is 0, the linking group $L^2$ is absent. When $L^2$ is absent, group Ar may be directly connected to the linking group M via a single bond. In an embodiment, $L^1$ and $L^2$ may each independently be a divalent $C_1$-$C_{30}$ linking group including an —O—, —C(=O)—O—, —O—C(=O)—, —C(=O)—NR—, or —O—C(=O)—NR— moiety, wherein R is H or a substituted or unsubstituted $C_1$-$C_5$ alkyl group. In another embodiment, group $L^2$ may include a substituted or unsubstituted $C_{1-30}$ alkylene group, a substituted or unsubstituted $C_{6-30}$ arylene group, a substituted or unsubstituted $C_{7-30}$ aralkylene group, or a combination comprising at least one of the foregoing groups.

The linking group M may be a substituted or unsubstituted, divalent $C_5$-$C_{30}$ or greater monocyclic, polycyclic, or fused polycyclic cycloaliphatic group, and may optionally include a heteroatom selected from O, S, N, F, or a combination including at least one of the foregoing heteroatoms. In an embodiment, group M may be a $C_{19}$ or less adamantyl group, a $C_{19}$ or less norbornanyl group, a $C_{7-20}$ lactone-containing group, a $C_{20}$ steroidal group, or $C_{20}$ or greater non-steroidal organic group. When m is 0, the linking group M is absent. When M is absent, the linking group $L^1$ may be directly connected to the linking group $L^2$ via a single bond. When l1 is 0 and m is 0, group Ar may be directly connected to the linking group $L^2$ via a single bond.

The zwitterionic photo-destroyable quencher represented by Formula (I) further includes group Y, which is an oxygen-containing anionic group. In an embodiment, Y may be C(=O)O, O, SO₂NH, or SO₃. For example, Y may be C(=O)O or O. When m is 0 and l2 is 0, the linking group $L^1$ may be directly connected to the anionic group Y via a single bond. When l1 is 0, m is 0, and l2 is 0, group Ar may be directly connected to the anionic group Y via a single bond.

In an embodiment, $l_1$ may be 0, $l_2$ may be 0, and m may be 0. In another embodiment, $l_1$ may be 1, $l_2$ may be 0 or 1, and m may be 0. In yet another embodiment, $l_1$ may be 1, $l_2$ may be 1, and m may be 1.

The compound of Formula (I) may be a sulfonium zwitterion represented by Formula (II):

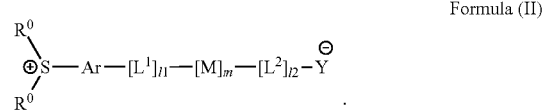

Formula (II)

In Formula (II), each R⁰ may be independently a $C_{1-30}$ alkyl group, a polycyclic or monocyclic $C_{3-30}$ cycloalkyl group, a polycyclic or monocyclic $C_{6-30}$ aryl group, or a combination comprising at least one of the foregoing, provided that at least one R⁰ is a polycyclic or monocyclic $C_{6-30}$ aryl group. Two groups R⁰ may be optionally connected to each other as to form a ring. In Formula (II), groups Ar, $L^1$, $L^2$, M, X, and variables l1, l2, and m may be the same as described above in connection with Formula (I).

The compound of Formula (I) may be an iodonium zwitterion represented by Formula (V):

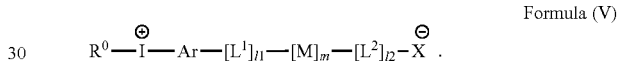

Formula (V)

In Formula (V), R⁰ may be a polycyclic or monocyclic $C_{6-30}$ aryl group. In Formula (V), groups Ar, $L^1$, $L^2$, M, X, and variables l1, l2, and m may be the same as described above in connection with Formula (II).

In an embodiment, the photo-destroyable quencher having Formula (I) may be represented by Formula (III) or Formula (IV):

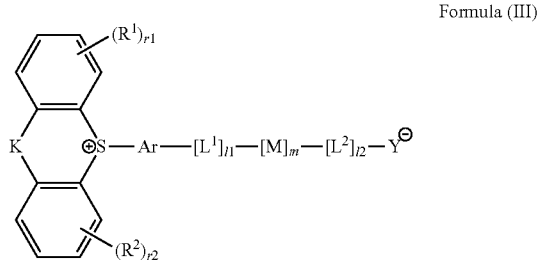

Formula (III)

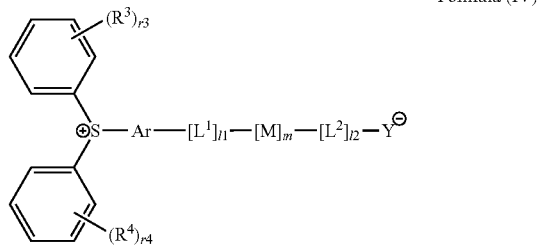

Formula (IV)

In Formula (III), two aromatic rings of the sulfonium cation are connected through a linker K. In an embodiment, K may be a single bond. In another embodiment, K may be a divalent connecting group selected from S, O, NR (wherein R is H or a substituted or unsubstituted $C_1$-$C_5$ alkyl group), S(=O), S(=O)$_2$, C(=O), C(=O)O, OC(=O), a substituted or unsubstituted C$_1$-C$_5$ alkylene group, or a combination thereof.

The aromatic rings of the constrained sulfonium cation may be substituted or unsubstituted with groups R$^1$ and R$^2$. R$^1$ and R$^2$ may each independently be a halogen, —CN, —OH, a C$_{1-10}$ alkyl group, a C$_{1-10}$ fluoroalkyl group, a C$_{1-10}$ alkoxy group, a C$_{1-10}$ fluoroalkoxy group, a C$_{3-10}$ cycloalkyl group, a C$_{3-10}$ fluorocycloalkyl group, a C$_{3-10}$ cycloalkoxy group, or a C$_{3-10}$ fluorocycloalkoxy group, each of which except a halogen, —CN, and —OH is substituted or unsubstituted, wherein two adjacent groups R$^1$ or two adjacent groups R$^2$ may optionally form a ring. Groups R$^1$ and R$^2$ are absent when r1 is 0 and r2 is 0. In some embodiments, the aromatic rings of the constrained sulfonium cation may include 1 to 4 groups R$^1$ and R$^2$. Thus, in Formula (II), r1 and r2 may each independently be 0, 1, 2, 3, or 4.

Formula (IV) represents an open sulfonium cation, in which two aromatic rings are not connected to each other. The aromatic rings of the open sulfonium cation may be substituted or unsubstituted with groups R$^3$ and R$^4$. R$^3$ and R$^4$ may each independently be a halogen, —CN, —OH, a C$_{1-10}$ alkyl group, a C$_{1-10}$ fluoroalkyl group, a C$_{1-10}$ alkoxy group, a C$_{1-10}$ fluoroalkoxy group, a C$_{3-10}$ cycloalkyl group, a C$_{3-10}$ fluorocycloalkyl group, a C$_{3-10}$ cycloalkoxy group, or a C$_{3-10}$ fluorocycloalkoxy group, each of which except a halogen, —CN, and —OH is substituted or unsubstituted, wherein two adjacent groups R$^3$ or two adjacent groups R$^4$ may optionally form a ring. Groups R$^3$ and R$^4$ are absent when r3 is 0 and r4 is 0. In some embodiments, the aromatic rings of the constrained sulfonium cation may include 1 to 5 groups R$^3$ and R$^4$. Thus, in Formula (II), r3 and r4 may each independently be 0, 1, 2, 3, 4, or 5.

Specific examples of the photo-destroyable quenchers may include:

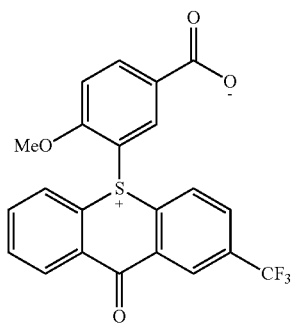

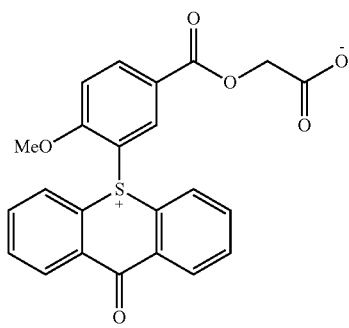

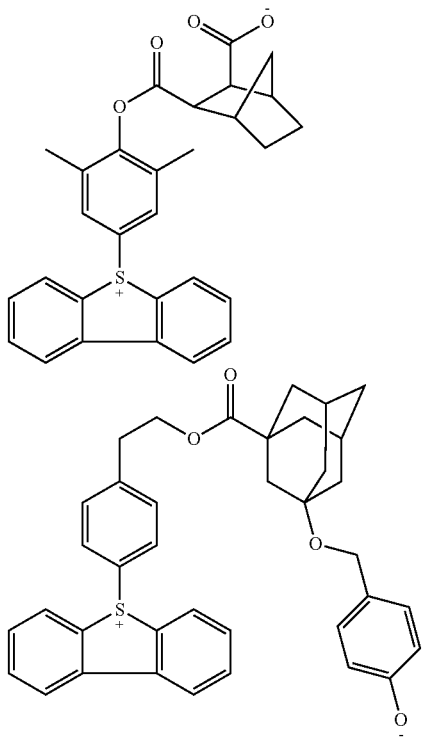

The photo-destroyable quencher according to the embodiments of the present invention can be formulated with a photoacid generator. The photoacid generator may be any suitable compound known in the art. For example, the photoacid generator may be a compound having Formula (VI):

$$G^+Z^- \qquad \text{Formula (VI)}$$

wherein G has the Formula (VII):

   Formula (VII)

In Formula (VII), X may be S or I. Each R$^0$ is attached to X and may independently be a C$_{1-30}$ alkyl group; a polycyclic or monocyclic C$_{3-30}$ cycloalkyl group; a polycyclic or monocyclic C$_{6-30}$ aryl group; or a combination comprising at least one of the foregoing. r5 may be 2 or 3, provided that when X is I, r5 is 2, and when X is S, r5 is 2 or 3. In Formula (VI), Z may include the anion of a sulfonic acid, a sulfonimide, or a sulfonamide.

The composition may further include a polymer and a solvent to form a photoresist composition. The polymer may be an acid-sensitive polymer. Where the combination is a polymer bound photoacid generator, an appropriately functionalized photoacid generator can be copolymerized with one or more monomers to form the copolymer, or the photoacid generator can be grafted onto the copolymer.

A copolymer useful for forming a photoresist in combination with the photoacid generator disclosed herein may include an acid-deprotectable (acid-sensitive) monomer, a base-soluble monomer, a dissolution rate modifying monomer, and an etch resistant monomer. Any such monomers or combinations of monomers are suitable for forming, for example, a 193 nm photoresist polymer. In an embodiment, a combination of monomers may be used, which include a (meth)acrylate monomer having an acid-deprotectable base soluble group, a (meth)acrylate monomer having a lactone functional group, a (meth)acrylate monomer having a base-soluble group, or a combination including at least one of the foregoing monomers. Other monomers, such as (meth) acrylate monomer for improving adhesion, etch resistance, and so on, may also be included.

Any acid-deprotectable monomer useful for forming a 193 nm photoresist polymer may be used. Exemplary acid-deprotectable monomers include, but are not limited to:

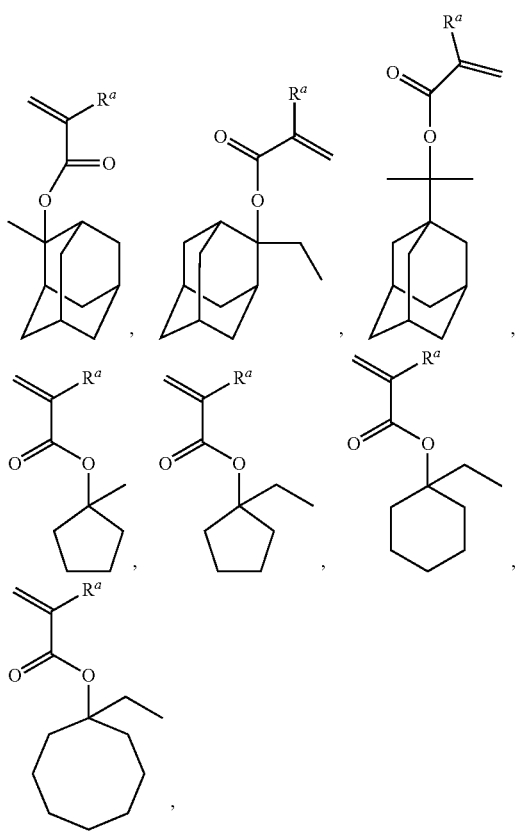

or a combination comprising at least one of the foregoing monomers, wherein $R^a$ is H, F, CN, $C_{1-10}$ alkyl, or $C_{1-10}$ fluoroalkyl.

Any lactone-containing monomer useful for forming a 193 nm photoresist polymer may be used. Exemplary lactone-containing monomers include, but are not limited to:

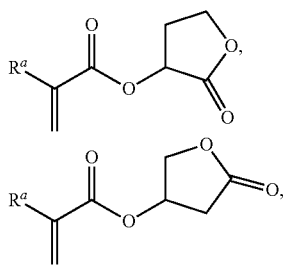

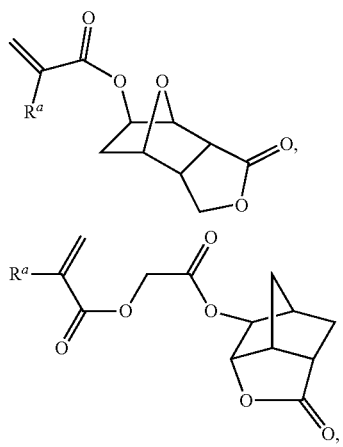

or a combination including at least one of the foregoing monomers, wherein $R^a$ is H, F, CN, a $C_{1-10}$ alkyl group, or a $C_{1-10}$ fluoroalkyl group.

Any base-soluble monomer useful for forming a 193 nm photoresist polymer may be used. Exemplary additional base-soluble (meth)acrylate monomers include, but are not limited to:

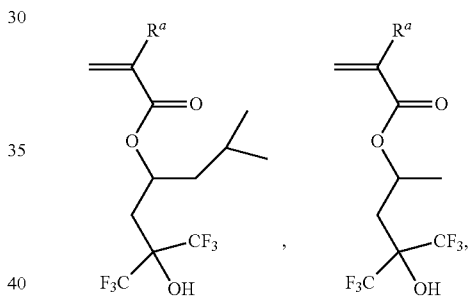

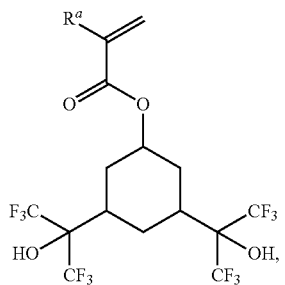

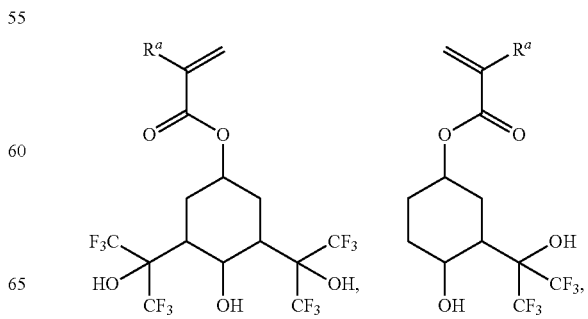

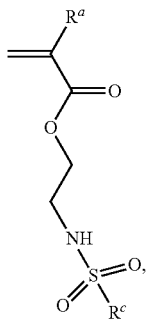

or a combination including at least one of the foregoing monomers, wherein $R^a$ is H, F, CN, a $C_{1-10}$ alkyl group, or a $C_{1-10}$ fluoroalkyl group, and $R^c$ is a $C_{1-4}$ perfluoroalkyl group.

The polymer may also include other monomers, including cage-structured monomers for enhancing etch resistance, with or without functional groups for improving adhesion. An exemplary adhesion-improving monomer may include:

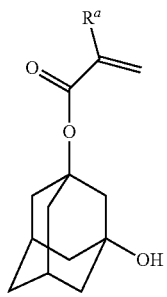

or a combination comprising the foregoing and at least one additional monomer, wherein $R^a$ is H, $C_{1-6}$ alkyl, or $CF_3$.

The photoacid generator may be combined with the copolymer, either in admixture, by copolymerization or both, to form a photoresist. The photoresist may optionally further include a second acid sensitive polymer and/or photoacid generator, an amine or an amide additive to adjust photospeed and/or acid diffusion, a solvent, and a surfactant.

The second acid-sensitive polymer may be any polymer suitable for formulating photoresists for use at 193 nm. Such acid-sensitive polymers may include an acid sensitive polymer including acid sensitive groups and lactone-containing groups, wherein the deprotection of the acid sensitive group on exposure to acid releases a base-soluble group. The acid-sensitive polymer may be a polymer-bound photoacid generator (PBP) wherein the photoacid generator repeat unit is an anion or a cation.

The photoresist composition may further include an amine or amide compound, referred to herein as a quencher. Quenchers may more broadly include, for example, compounds which are hydroxides, carboxylates, amines, imines, and amides. In an embodiment, a useful quencher is an amine, an amide, or a combination comprising at least one of the foregoing. For example, such quenchers may include $C_{1-30}$ organic amines, imines, or amides, or may be a $C_{1-30}$ quaternary ammonium salt of a strong base (for example, a hydroxide or alkoxide) or a weak base (for example, a carboxylate). Exemplary quenchers may include amines such as Troger's base, a hindered amine such as diazabicycloundecene (DBU) or diazabicyclononene (DBN), N-pro-tected amines such as N-t-butylcarbonyl-1,1-bis(hydroxymethyl)-2-hydroxyethylamine (TBOC-TRIS), or ionic quenchers including quaternary alkyl ammonium salts such as tetrabutylammonium hydroxide (TBAH) or tetrabutyl ammonium lactate.

Other components of the photoresist may include solvents and surfactants.

Solvents generally suitable for dissolving, dispensing, and coating the components may include anisole, alcohols including ethyl lactate, methyl 2-hydroxybutyrate (HBM), 1-methoxy-2-propanol (also referred to as propylene glycol methyl ether, PGME), and 1-ethoxy-2 propanol, esters including n-butylacetate, 1-methoxy-2-propyl acetate (also referred to as propylene glycol methyl ether acetate, PGMEA), methoxyethoxypropionate, ethoxyethoxypropionate, and gamma-butyrolactone, ketones including cyclohexanone and 2-heptanone, and a combination comprising at least one of the foregoing solvents.

Surfactants may include fluorinated and non-fluorinated surfactants, and may, for example, be non-ionic. Exemplary fluorinated non-ionic surfactants may include perfluoro $C_4$ surfactants such as FC-4430 and FC-4432 surfactants, available from 3M Corporation; and fluorodiols such as POLYFOX PF-636, PF-6320, PF-656, and PF-6520 fluorosurfactants from Omnova.

The photo-destroyable quencher may be present in the photoresist in an amount of 0 to 20 percent by weight (wt %), for example, 1 to 5 wt %, based on the total weight of the solids. The photoacid generator may be present in the photoresist in an amount of 0.01 to 35 wt %, for example, 0.1 to 20 wt %, based on the total weight of the solids. Where a polymer bound photoacid generator is used, the polymer bound photoacid generator as the corresponding monomer is present in the same amount. The copolymer may be present in an amount of 50 to 99 wt %, for example, 55 to 95 wt %, in another example, 60 to 90 wt %, and in still another example, 65 to 90 wt % based on the total weight of the solids. It will be understood that the term "polymer" used in this context of a component in a photoresist may mean only the copolymer disclosed herein, or a combination of the polymer with another polymer useful in a photoresist. A surfactant may be included in an amount of 0.01 to 5 wt %, for example, 0.1 to 4 wt %, and in another example, 0.2 to 3 wt %, based on the total weight of the solids. A quencher may be included in a relatively small amount of, for example, from 0.03 to 5 wt % based on the total weight of the solids. Other additives such as embedded barrier layer (EBL) materials for immersion lithography applications may be included in amounts of less than or equal to 30 wt %, for example, less than or equal to 20%, or in another example, less than or equal to 10%, based on the total weight of the solids. The total solids content for the photoresist composition may be 0.5 to 50 wt %, for example, 1 to 45 wt %, and in another example, 2 to 40 wt %, and still in another example, 5 to 35 wt %, based on the total weight of the solids and solvent. It will be understood that the solids may include a copolymer, a photoacid generator, a quencher, a surfactant, and any optional additives, exclusive of the solvent.

The photoresist composition disclosed herein may be used to form a film comprising the photoresist composition, where the film on the substrate constitutes a coated substrate. Such a coated substrate may include: (a) a substrate having one or more layers to be patterned on a surface thereof, and (b) a layer of the photoresist composition over the one or more layers to be patterned. For example, patterning may be carried out using ultraviolet radiation at a wavelength of less than 248 nm, and in particular, at 193 nm. The patternable film thus includes the photoacid generator of Formula (I).

A method of forming an electronic device therefore includes: (a) coating a substrate having a layer comprising a polymer (which may be an acid-sensitive polymer), a photoacid generator, and a photo-destroyable quencher having Formula (I); (b) pattern-wise exposing the photoresist composition layer to activating radiation; and (c) developing the exposed photoresist composition layer to provide a resist relief image. For example, the radiation is 193 nm or 248 nm radiation.

Substrates may be of any dimension and shape, and may, for example, be those useful for photolithography, such as silicon, silicon dioxide, silicon-on-insulator (SOI), strained silicon, gallium arsenide, coated substrates including those coated with silicon nitride, silicon oxynitride, titanium nitride, tantalum nitride, ultrathin gate oxides such as hafnium oxide, metal or metal coated substrates including those coated with titanium, tantalum, copper, aluminum, tungsten, alloys thereof, and combinations thereof. For example, the surfaces of substrates herein include critical dimension layers to be patterned including, for example, one or more gate-level layers or other critical dimension layer on the substrates for semiconductor manufacture. Such substrates may, for example, include silicon, SOI, strained silicon, and other such substrate materials, formed as circular wafers having dimensions such as, for example, 200 mm, 300 mm, or larger in diameter, or other dimensions useful for wafer fabrication production.

The novel fused photo-destroyable quenchers may be synthesized utilizing the corresponding oxygen-containing anions to form the zwitterionic species with the sulfonium cation. In this method, a sulfonium bromide or iodide which is composed of either a benzoic acid, sulfonic acid, or phenolic moiety may be exposed to silver oxide in a solvent. After neutralization of the acidic species (carboxylic acid, sulfonic acid, or phenol) and precipitation of silver bromide/iodide, the fused photo-destroyable quenchers may be easily isolated by filtration and solvent removal. Each of these synthetic routes (carboxylic acid, sulfonic acid, or phenol) are robust, scalable, and may be applicable to a variety of compounds contain a benzoic acid, a sulfonic acid, or phenolic moiety.

The present inventive concept is further illustrated by the following examples. All compounds and reagents used herein are available commercially except where a procedure is provided below.

EXAMPLES

Example 1: 3-(5H-Dibenzo[b,d]thiophenium-5-yl)-4-methoxybenzoate

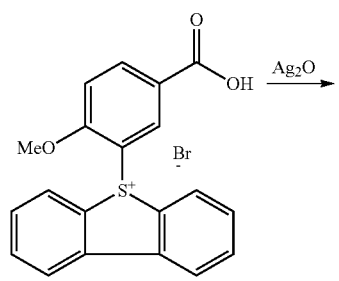

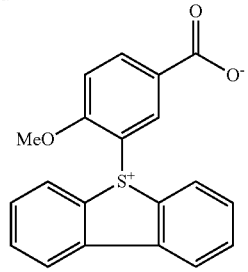

A mixture of 5-(5-carboxy-2-methoxyphenyl)-5H-dibenzo[b,d]thiophenium iodide (1.00 g, 2.16 mmol) and silver oxide (2.16 mmol, 0.251 g) was dissolved in methanol (30 mL) and stirred at room temperature overnight. The precipitate was filtered and the methanol was concentrated. The residue was diluted with methanol (30 mL) and concentrated. The product was precipitated from methyl tert-butyl ether (MTBE) to afford the title compound (0.723 g, 84%) as a white solid.

1H NMR (500 MHz, (CD$_3$)$_2$CO) δ (ppm): 8.39 (d, J=8 Hz, 2H), 8.25 (dt, J=8, 1.5 Hz, 1H), 8.17 (d, J=8 Hz, 2H), 7.94 (t, J=7.5 Hz, 2H), 7.71-7.77 (m, 3H), 7.32 (dd, J=8.5, 1.5 Hz, 1H), 3.99 (s, 3H).

Example 2: 4-(Diphenylsulfonio)phenolate

A mixture of (4-hydroxyphenyl)diphenylsulfonium iodide (1.00 g, 2.46 mmol) and silver oxide (2.46 mmol, 0.285 g) were dissolved in methanol (30 mL) and stirred at room temperature overnight. The precipitate was filtered and the methanol was concentrated. The residue was diluted with methanol (30 mL) and concentrated. The product was precipitated from a mixture of MTBE and heptane to afford the title compound (0.690 g, 100%) as a hydroscopic white solid.

1H NMR (500 MHz, (CD$_3$)$_2$CO) δ (ppm): 7.58-7.78 (m, 10H), 7.17 (dd, J=9.5, 2 Hz, 2H), 6.18 (dd, J=9, 2 Hz, 2H).

Example 3: Preparation of Polymer with Acid Generator Units

The heel solution was made by dissolving 2-phenylpropan-2-yl methacrylate (0.39 g), 2-oxotetrahydrofuran-3-yl methacrylate (0.33 g), 3,5-bis(1,1,1,3,3,3-hexafluoro-2-hydroxypropan-2-yl)cyclohexyl methacrylate (0.57 g) and 5-(4-(2-(1-ethylcyclopentyloxy)-2-oxoethoxy)-3,5-dimethylphenyl)-5H-dibenzo[b,d]thiophenium 1,1-difluoro-2-(methacryloyloxy)ethanesulfonate (0.31 g) in 12.81 g acetonitrile/tetrahydrofuran (2/1 volume to volume, v/v). The feed solution was prepared by dissolving 2-phenylpropan-2-yl methacrylate (185.54 g, 0.967 mol), 2-oxotetrahydrofuran-3-yl methacrylate (204.27 g, 1.26 mol), 3,5-bis(1,1,1,3,3,3-hexafluoro-2-hydroxypropan-2-yl)cyclohexyl methacrylate (127.98 g, 0.29 mol) and 5-(4-(2-(1-ethylcyclopentyloxy)-2-oxoethoxy)-3,5-dimethylphenyl)-5H-dibenzo[b,d]thiophenium 1,1-difluoro-2-(methacryloyloxy) ethanesulfonate (81.5 g, 0.132 mol) in 606 g ethyl lactate:γ-butyryl lactone (30/70 v/v). The initiator solution was prepared by dissolving 65.96 g initiator (V-65) in 66 g acetonitrile/tetrahydrofuran (2/1 v/v). The polymerization was carried out in a 2 L 3-neck round bottom flask fitted with a water condenser and a thermometer to monitor the reaction in the flask. The contents were stirred using an overhead stirrer. The reactor was charged with the heel solution and the contents were heated to 75° C. The feed solution and the initiator solution were fed into the reactor using syringe pump over a 4 hour time period. The contents were then stirred for additional 2 hours, whereby, the reaction was quenched using hydroquinone (2.0 g). The contents were cooled to room temperature and precipitated twice out of 10-fold excess (by weight) IPE/MeOH 95/5 (weight to weight, w/w). The polymer obtained was dried in vacuo after each precipitation step at 50° C. for 24 hours to yield 500 g of the polymer.

Example 4: Preparation of Polymer with Acid Generator Units

The same process and mole ratio used in Example 3 was used in the preparation of the polymer in the present example, except 5-(phenyl)-5H-dibenzo[b,d]thiophenium 1,1-difluoro-2-(methacryloyloxy)ethanesulfonate was used in place of 5-(4-(2-(1-ethylcyclopentyloxy)-2-oxoethoxy)-3,5-dimethylphenyl)-5H-dibenzo[b,d]thiophenium 1,1-difluoro-2-(methacryloyloxy)ethanesulfonate:

Example 5: Preparation of Photoacid Generator

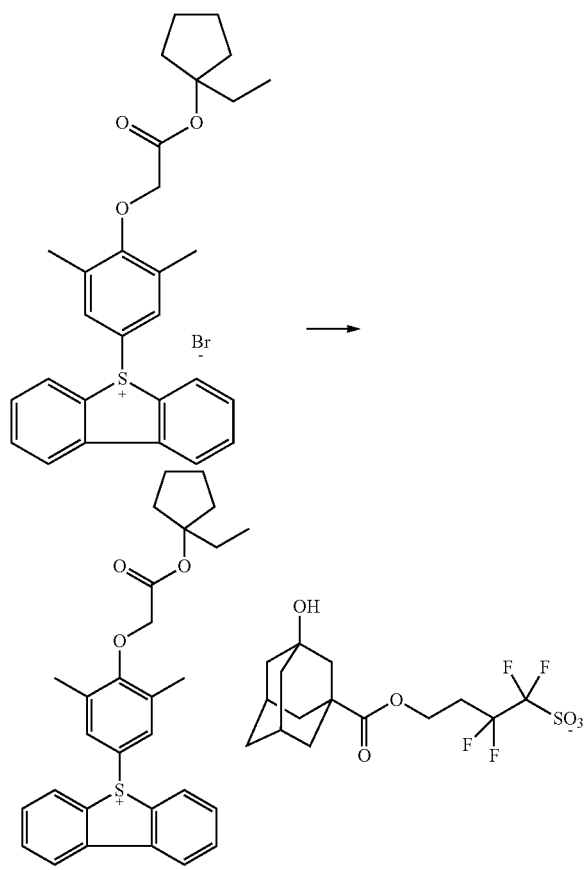

5-(4-(2-(1-ethylcyclopentyloxy)-2-oxoethoxy)-3,5-dimethylphenyl)-5H-dibenzo[b,d]thiophenium bromide (2.00 g, 3.71 mmol) and sodium 3-hydroxyadamantane-acetoxy-1,1,2,2-tetrafluorobutane-1-sulfonate (1.61 g, 3.78 mmol) were dissolved in dichloromethane (100 mL) and water (100 mL) and stirred at room temperature overnight. The dichloromethane layer was separated and the aqueous phase was washed with dichloromethane (3×100 mL). The combined organic layers were washed with water (4×200 mL), concentrated in vacuo and residual water was removed via azeotrope with acetonitrile (2×200 mL) to afford the title compound (2.90 g, 91%) as a white solid.

$^1$H NMR (500 MHz, $(CD_3)_2CO$) δ: 8.52 (d, J=8 Hz, 2H), 8.34 (d, J=8.5 Hz, 2H), 8.01 (t, J=7.5 Hz, 2H), 7.08 (t, J=7.5 Hz, 2H), 7.51 (s, 2H), 4.55 (s, 2H), 4.32 (t, J=6.5 Hz, 2H), 3.60 (br s, OH), 2.72 (tt, J=14, 6.5 Hz, 2H), 2.29 (s, 6H), 2.12-2.20 (m, 2H), 2.00 (q, J=7 Hz, 2H), 1.50-1.82 (m, 12H), 0.84 (t, J=7 Hz, 3H).

Example 6: Photoresist Formulation Including Photo-Destroyable Quencher

A positive-tone photoresist composition was prepared by combining 10.297 g of a 10 wt % solution of the polymer obtained in Example 4 in ethyl lactate, 10.047 g of a 2 wt % solution of the acid listed in Example 5 in ethyl lactate, 0.586 g of a 0.5 wt % solution of tetrakis(2-hydroxypropyl)ethylenediamine in ethyl lactate, 0.945 g of a 2 wt % solution of the compound prepared as described in Example 1 in ethyl lactate, 0.206 g of a 0.5 wt % solution of fluorinated surfactant (Omnova PF656) in ethyl lactate, 13.005 g of ethyl lactate and 14.625 g of 2-hydroxyisobutyric acid methyl ester. The formulated resist was passed through a 0.01 μm PTFE filter. The prepared resist is spin coated onto a silicon wafer, soft baked to remove carrier solvent and exposed through a photomask to EUV radiation. The imaged resist layer is then baked at 110° C. for 60 seconds and then developed with an aqueous alkaline composition.

Comparative Example: Photoresist Formulation without Photo-Destroyable Quencher

A positive-tone photoresist composition was prepared by combining 10.297 g of a 10 wt % solution of the polymer obtained in Example 4 in ethyl lactate, 10.047 g of a 2 wt % solution of the acid listed in Example 5 in ethyl lactate, 0.586 g of a 0.5 wt % solution of tetrakis(2-hydroxypropyl)ethylenediamine in ethyl lactate, 0.206 g of a 0.5 wt % solution of fluorinated surfactant (Omnova PF656) in ethyl lactate, 13.005 g of ethyl lactate and 14.625 g of 2-hydroxyisobutyric acid methyl ester. The formulated resist was passed through a 0.01 μm PTFE filter. The prepared resist is spin coated onto a silicon wafer, soft baked to remove carrier solvent and exposed through a photomask to EUV radiation. The imaged resist layer is then baked at 110° C. for 60 seconds and then developed with an aqueous alkaline composition.

The data comparing E-size and local critical dimension uniformity (LCDU) number of the formulations prepared according to Example 5 and Comparative Example are summarized in Table 1.

|  | E-size (mJ/cm$^2$) | LCDU (nm) |
| --- | --- | --- |
| Comparative Example | □ | □ |
| Example 6 | ● | ◆ | wherein □ is reference, ● is improvement by >10%, and ◆ is the same as reference.

It was found that the E-size value of the formulation including the photo-destroyable quencher (Example 6) was improved by 10% compared to that value of the formulation having no photo-destroyable quencher (Comparative Example). This improvement was achieved without sacrificing the LCDU value of the formulation.

While this disclosure has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

The invention claimed is:

1. A photo-destroyable quencher having Formula (I):

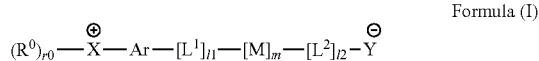

Formula (I)

wherein

X is S or I, each $R^0$ is attached to X, and is independently a $C_{1-30}$ alkyl group, a polycyclic or monocyclic $C_{3-30}$ cycloalkyl group, a polycyclic or monocyclic $C_{6-30}$ aryl group, or a combination comprising at least one of the foregoing, provided that at least one $R^0$ is a polycyclic or monocyclic $C_{6-30}$ aryl group;

r0 is 1 or 2, provided that when X is I, r0 is 1, and when X is S, r0 is 2, wherein when X is S, groups $R^0$ are optionally connected to each other so as to form a ring; and Ar is a substituted or unsubstituted divalent $C_6$-$C_{30}$ aromatic group;

$L^1$ and $L^2$ are each independently a divalent $C_1$-$C_{30}$ linking group optionally comprising a heteroatom comprising O, S, N, F, or a combination comprising at least one of the foregoing heteroatoms;

M is a substituted or unsubstituted, divalent $C_5$-$C_{30}$ or greater monocyclic, polycyclic, or fused polycyclic cycloaliphatic group, optionally comprising a heteroatom comprising O, S, N, F, or a combination comprising at least one of the foregoing;

Y is an oxygen-containing anionic group, provided that when X is S, Y is C(=O)O, O, or SO$_2$NH; and $l_1$, $l_2$, and m are each independently an integer of 0 or 1.

2. The photo-destroyable quencher according to claim 1, wherein the compound of Formula (I) is represented by Formula (II):

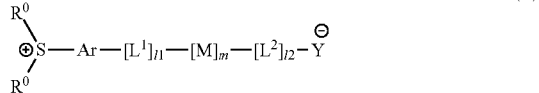

Formula (II)

wherein each $R^0$ is independently a $C_{1-30}$ alkyl group, a polycyclic or monocyclic $C_{3-30}$ cycloalkyl group, a polycyclic or monocyclic $C_{6-30}$ aryl group, or a combination comprising at least one of the foregoing, provided that at least one $R^0$ is a polycyclic or monocyclic $C_{6-30}$ aryl group;

groups $R^0$ are optionally connected to each other so as to form a ring; and

Ar is a substituted or unsubstituted divalent $C_6$-$C_{30}$ aromatic group;

$L^1$ and $L^2$ are each independently a divalent $C_1$-$C_{30}$ linking group optionally comprising a heteroatom comprising O, S, N, F, or a combination comprising at least one of the foregoing heteroatoms;

M is a substituted or unsubstituted, divalent $C_5$-$C_{30}$ or greater monocyclic, polycyclic, or fused polycyclic cycloaliphatic group, optionally comprising a heteroatom comprising O, S, N, F, or a combination comprising at least one of the foregoing;

Y is C(=O)O, O, or SO$_2$NH; and $l_1$, $l_2$, and m are each independently an integer of 0 or 1.

3. The photo-destroyable quencher according to claim 2, wherein each $R^0$ is a polycyclic or monocyclic $C_{6-30}$ aryl group.

4. The photo-destroyable quencher according to claim 1, wherein the photo-destroyable quencher having Formula (I) is represented by Formula (III) or Formula (IV):

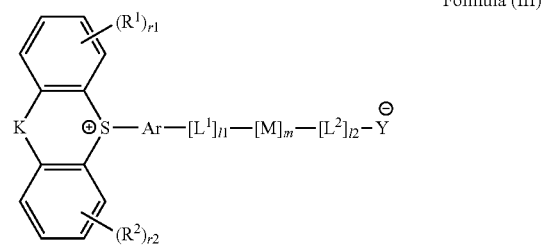

Formula (III)

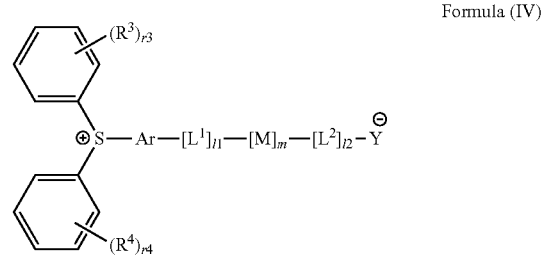

Formula (IV)

wherein

K is a single bond or a divalent connecting group selected from S, O, NR (wherein R is H or a substituted or unsubstituted $C_1$-$C_5$ alkyl group), S(=O), S(=O)$_2$, C(=O), C(=O)O, OC(=O), a substituted or unsubstituted $C_1$-$C_5$ alkylene group, or a combination thereof;

Ar is a substituted or unsubstituted divalent $C_6$-$C_{30}$ aromatic group;

$L^1$ and $L^2$ are each independently a divalent $C_1$-$C_{30}$ linking group optionally comprising a heteroatom comprising O, S, N, F, or a combination comprising at least one of the foregoing heteroatoms;

M is a substituted or unsubstituted, divalent $C_5$-$C_{30}$ or greater monocyclic, polycyclic, or fused polycyclic cycloaliphatic group, optionally comprising a heteroatom comprising O, S, N, F, or a combination comprising at least one of the foregoing;

Y is C(=O)O, O, or SO$_2$NH;

$R^1$ to $R^4$ are each independently a halogen, —CN, —OH, a $C_{1-10}$ alkyl group, a $C_{1-10}$ fluoroalkyl group, a $C_{1-10}$ alkoxy group, a $C_{1-10}$ fluoroalkoxy group, a $C_{3-10}$ cycloalkyl group, a $C_{3-10}$ fluorocycloalkyl group, a $C_{3-10}$ cycloalkoxy group, or a $C_{3-10}$ fluorocycloalkoxy group, each of which except a halogen, —CN, and —OH is substituted or unsubstituted, wherein two adjacent $R^1$, two adjacent $R^2$, two adjacent $R^3$, or two adjacent $R^4$ optionally form a ring;

$l_1$, $l_2$, and m are each independently an integer of 0 or 1;

$r_1$ and $r_2$ are each independently an integer of 0 to 4; and $r_3$ and $r_4$ are each independently an integer of 0 to 5.

5. The photo-destroyable quencher according to claim 1, wherein Ar is a substituted or unsubstituted phenylene group.

6. The photo-destroyable quencher according to claim 1, wherein when X is I, Y is C(=O)O, O, $SO_2NH$, or $SO_3$.

7. The photo-destroyable quencher according to claim 1, wherein $L^1$ and $L^2$ are each independently a divalent $C_1$-$C_{30}$ linking group comprising an —O—, —C(=O)—O—, —O—C(=O)—, —C(=O)—NR—, or —O—C(=O)—NR— moiety, wherein R is H or a substituted or unsubstituted $C_1$-$C_5$ alkyl group.

8. The photo-destroyable quencher according to claim 1, wherein M is a $C_{19}$ or less adamantyl group, a $C_{19}$ or less norbornanyl group, a $C_{7-20}$ lactone-containing group, a $C_{20}$ steroidal group, or $C_{20}$ or greater non-steroidal organic group.

9. The photo-destroyable quencher according to claim 1, wherein (i) $l_1$ is 0, $l_2$ is 0, and m is 0;

(ii) $l_1$ is 1, $l_2$ is 0 or 1, and m is 0; or (iii) $l_1$ is 1, $l_2$ is 1, and m is 1.

10. The photo-destroyable quencher according to claim 1, wherein $L^2$ comprises a substituted or unsubstituted $C_{1-30}$ alkylene group, a substituted or unsubstituted $C_{6-30}$ arylene group, a substituted or unsubstituted $C_{7-30}$ aralkylene group, or combination comprising at least one of the foregoing.

11. A composition comprising:
an acid-sensitive polymer;
a photoacid generator; and
the photo-destroyable quencher of claim 1.

12. A coated substrate comprising: (a) a substrate having one or more layers to be patterned on a surface thereof; and (b) a layer of the composition of claim 11 disposed over the one or more layers to be patterned.

13. A method of making a relief image, the method comprising
coating a substrate having a layer comprising
an acid-sensitive polymer,
a photoacid generator, and
a photo-destroyable quencher having Formula (I):

Formula (I)

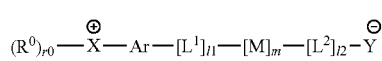

wherein
X is S or I,
each $R^0$ is attached to X, and is independently a $C_{1-30}$ alkyl group, a polycyclic or monocyclic $C_{3-30}$ cycloalkyl group, a polycyclic or monocyclic $C_{6-30}$ aryl group, or a combination comprising at least one of the foregoing, provided that at least one $R^0$ is a polycyclic or monocyclic $C_{6-30}$ aryl group;
r0 is 1 or 2, provided that when X is I, r0 is 1, and when X is S, r0 is 2, wherein when X is S, groups $R^0$ are optionally connected to each other so as to form a ring; and
Ar is a substituted or unsubstituted divalent $C_6$-$C_{30}$ aromatic group;
$L^1$ and $L^2$ are each independently a divalent $C_1$-$C_{30}$ linking group optionally comprising a heteroatom comprising O, S, N, F, or a combination comprising at least one of the foregoing heteroatoms;

M is a substituted or unsubstituted, divalent $C_5$-$C_{30}$ or greater monocyclic, polycyclic, or fused polycyclic cycloaliphatic group, optionally comprising a heteroatom comprising O, S, N, F, or a combination comprising at least one of the foregoing;

Y is an oxygen-containing anionic group, provided that when X is S, Y is C(=O)O, O, or $SO_2NH$; and $l_1$, $l_2$, and m are each independently an integer of 0 or 1, pattern-wise exposing the composition layer to activating radiation; and developing the exposed photoresist composition layer to provide a resist relief image.

14. A photo-destroyable quencher having Formula (II-A):

Formula (II-A)

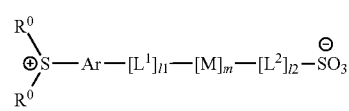

wherein
each $R^0$ is independently a $C_{1-30}$ alkyl group, a polycyclic or monocyclic $C_{3-30}$ cycloalkyl group, a polycyclic $C_{6-30}$ aryl group, a monocyclic $C_{6-30}$ aryl group substituted with halogen, or a combination comprising at least one of the foregoing, provided that at least one $R^0$ is a polycyclic $C_{6-30}$ aryl group or a monocyclic $C_{6-30}$ aryl group substituted with halogen;

groups $R^0$ are optionally connected to each other so as to form a ring; and

Ar is a substituted or unsubstituted divalent $C_6$-$C_{30}$ aromatic group;

$L^1$ and $L^2$ are each independently a divalent $C_1$-$C_{30}$ linking group optionally comprising a heteroatom comprising O, S, N, F, or a combination comprising at least one of the foregoing heteroatoms;

M is a substituted or unsubstituted, divalent $C_5$-$C_{30}$ or greater monocyclic, polycyclic, or fused polycyclic cycloaliphatic group, optionally comprising a heteroatom comprising O, S, N, F, or a combination comprising at least one of the foregoing; and $l_1$, $l_2$, and m are each independently an integer of 0 or 1.

15. A composition comprising:
an acid-sensitive polymer;
a photoacid generator; and
the photo-destroyable quencher of claim 14.

16. A coated substrate comprising: (a) a substrate having one or more layers to be patterned on a surface thereof; and (b) a layer of the composition of claim 15 disposed over the one or more layers to be patterned.

17. A method of making a relief image, the method comprising coating a substrate having a layer comprising
an acid-sensitive polymer,
a photoacid generator, and
a photo-destroyable quencher having Formula (II-A):

Formula (II-A)

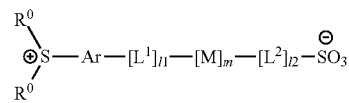

wherein each $R^o$ is independently a $C_{1-30}$ alkyl group, a polycyclic or monocyclic $C_{3-30}$ cycloalkyl group, a polycyclic $C_{6-30}$ aryl group, a monocyclic $C_{6-30}$ aryl group substituted with halogen, or a combination comprising at least one of the foregoing, provided that at least one $R^o$ is a polycyclic $C_{6-30}$ aryl group or a monocyclic $C_{6-30}$ aryl group substituted with halogen;

groups $R^o$ are optionally connected to each other so as to form a ring; and

Ar is a substituted or unsubstituted divalent $C_6$-$C_{30}$ aromatic group;

$L^1$ and $L^2$ are each independently a divalent $C_1$-$C_{30}$ linking group optionally comprising a heteroatom comprising O, S, N, F, or a combination comprising at least one of the foregoing heteroatoms;

M is a substituted or unsubstituted, divalent $C_5$-$C_{30}$ or greater monocyclic, polycyclic, or fused polycyclic cycloaliphatic group, optionally comprising a heteroatom comprising O, S, N, F, or a combination comprising at least one of the foregoing; and $l_1$, $l_2$, and m are each independently an integer of 0 or 1, pattern-wise exposing the composition layer to activating radiation; and developing the exposed photoresist composition layer to provide a resist relief image.

* * * * *